United States Patent [19]

Pullukat

[11] 4,020,092
[45] Apr. 26, 1977

[54] COMPOUNDS BIS(TRIBUTYLTIN)CHROMATE AND BIS(TRIPHENYLTIN)CHROMATE

[75] Inventor: Thomas J. Pullukat, Des Plaines, Ill.
[73] Assignee: Chemplex Company, Rolling Meadows, Ill.
[22] Filed: Nov. 27, 1974
[21] Appl. No.: 527,602

Related U.S. Application Data

[62] Division of Ser. No. 414,177, Nov. 8, 1973, Pat. No. 3,876,554.
[52] U.S. Cl. .......................... 260/429.7; 252/431 R
[51] Int. Cl.$^2$ ........................................... C07F 7/22
[58] Field of Search ............. 260/429.7; 252/431 R

[56] References Cited

UNITED STATES PATENTS

| 3,324,101 | 6/1967 | Baker et al. | 252/431 R X |
| 3,468,865 | 9/1969 | Santiago | 252/431 R X |
| 3,642,749 | 2/1972 | Johnson et al. | 252/431 R X |
| 3,847,957 | 11/1974 | Boone | 260/429.5 |
| 3,884,832 | 5/1975 | Pullukat et al. | 252/431 R |

OTHER PUBLICATIONS

Sawyer, Organotin Compounds, Marcel Dekker, Inc. N.Y. vol. 2 pp. 278–279 (1971); vol. 1 pp. 130–131 (1971).

Chemical Abstracts, 82, 147951n (1975).

Primary Examiner—Helen M. S. Sneed
Attorney, Agent, or Firm—Wegner, Stellman, McCord, Wiles & Wood

[57] ABSTRACT

A catalyst system for the polymerization of at least one 1-olefin comprising a mixture of a bis-trihydrocarbyltinchromate essentially of the formula:

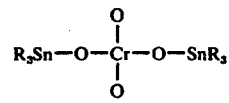

and cocatalytic amounts of an alkyl aluminum compound of the formula $R_aAlX_b$ in each of which formula each R is a hydrocarbyl radical containing from 1 to about 14 carbon atoms and all R's are the same or different, X is a halogen or an alkoxy group, $a$ is an integer of 1–3, $b$ is an integer of 0–2 and the sum of $a$ and $b$ is 3. The disclosure also includes the method of polymerizing at least one such olefin which comprises contacting the olefin under polymerizing conditions with the above catalyst system.

3 Claims, No Drawings

1

COMPOUNDS BIS(TRIBUTYLTIN)CHROMATE AND BIS(TRIPHENYLTIN)CHROMATE

This is a division of application Ser. No. 414,177 filed Nov. 8, 1973, now U.S. Pat. No. 3,876,554.

BACKGROUND OF THE INVENTION

It is well known that 1-olefins can be polymerized either alone or in combinations of two or more with complex catalyst systems containing two or more independent components. For example, the Ziegler type catalysts use a transition metal compound and a reducing agent that is normally a compound of a metal in Group I, II or III of the Periodic Table. Such catalysts, as is known, require special handling procedures and they are corrosive to the polymerization equipment. The catalyst residue left in the polymer normally contains halides and they have to be removed. Another type of olefin polymerization system is the well known Phillips process. It contains chromium oxides supported on carriers like silica. This type of catalyst requires a special high temperature activating step and is susceptible to low levels of poisons.

Recently a different type of olefin polymerization catalyst has been disclosed. In U.S. Pat. Nos. 3,324,095, 3,324,101 and 3,468,865 are described a catalyst system consisting of an organosilyl chromate and an aluminum alkyl. In U.S. Pat. No. 3,493,554 is described a bis(diorgano) chromate-reducing agent system. The organo chromates and silyl chromates have the disadvantage of being not so stable. In fact, some silyl chromates are known to explode violently.

DESCRIPTION OF THE PREFERRED EMBODIMENTS

I have discovered that mixtures of organotin chromate and alkyl aluminum compounds can be used in a catalyst system for the polymerization of at least one 1-olefin of which ethylene is an excellent example.

The tin chromates employed herein are the bistrihydrocarbyltinchromates of the formula:

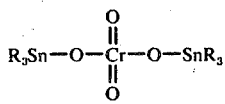

wherein R is a hydrocarbyl group containing from 1 to about 14 carbon atoms, preferably from about 3 to about 10 carbon atoms. Illustrative thereof are methyl, ethyl, propyl, iso-propyl, n-butyl, iso-butyl, n-phenyl, iso-pentyl, t-pentyl, hexyl, 2-methylpentyl, heptyl, octyl, 2-ethylhexyl, nonyl, decyl, hendecyl, dodecyl, tridecyl, tetradecyl, benzyl, phenethyl, p-methyl-benzyl, phenyl, tolyl, xylyl, naphthyl, ethylphenyl, methylnaphthyl, dimethylnaphthyl and the like. Illustrative of the preferred tinchromates but by no means exhaustive or complete of those which can be employed in this process are such compounds as:

Bis-trimethyltinchromate
Bis-triethyltinchromate
Bis-tributyltinchromate
Bis-triisopentyltinchromate
Bis-tri-2-ethylhexyltinchromate
Bis-tridecyltinchromate
Bis-tri(tetradecyl) tinchromate
Bis-tribenzyltinchromate
Bis-triphenethyltinchromate
Bis-triphenyltinchromate
Bis-tritolyltinchromate
Bis-trixylyltinchromate
Bis-trinaphthyltinchromate
Bis-triethylphenyltinchromate
Bis-trimethylnaphthyltinchromate
Polydiphenyltinchromate
Polydiethyltinchromate, and the like While both the aryl- and alkyl-substituted tinchromates can be used, it is to be noted that the aryl-tinchromates are more active and easier to prepare.

It is possible in this invention to conduct the olefin polymerization with the catalytic system of tinchromate-aluminum alkyl dissolved in an inert solvent or to have them in a finely divided or dispersed phase in the organic solvent reaction medium. Similarly, they can be employed deposited on or adsorbed on an insoluble support in the same manner by the use of a finely divided insoluble organic material such as silica, alumina, silica-alumina mixtures and like inorganic materials of large surface area. It is by this latter embodiment of the invention that outstanding results are secured in polymerization rates and yields of polymer with this catalytic system without the need for catalyst separation or purification of the polymer to separate catalyst residues.

Preferably, when employed as a solid catalyst or when employed deposited or adsorbed on a solid insoluble support, there should be large surface areas for greatest contact of the catalyst with the monomer. Hence, it is highly advantageous that solid catalysts be finely divided, considering the desirability or possibility of later separation by filtration or other catalyst removal steps, if desired. Preferably, porous supports having large surface areas for the adsorption and/or deposition of the tinchromates such as in the order of 50 to 100square meters or more per gram are employed. This provides for greater ease of contact of the olefin monomer with the catalyst. Particle size of porous supports is not critical in this invention but can provide economic and materials handling benefits, depending upon te recovery techniques employed.

In this embodiment of the invention it is highly desirable that the inert support be completely dried and freed of moisture and extraneous liquids before being contacted with the tinchromate. This is normally provided by a simple heating or pre-drying of the catalyst support with an inert gas prior to use herein.

Drying or activation of the support can be accomplished at nearly any temperature up to about its sintering temperature for a perid of time at least sufficient to remove the adsorbed water but avoiding that which will remove all of the chemically bound water. Desirably, an inert gas stream through the support during the drying aids in the displacement. Temperatures of from about 100° C. to 900° C. for a short period of about two hours or so should be sufficient if a well dried inert gas is used and the temperature not be permitted to get so high as to remove the chemically bound hydroxyl groups from the surface of the support. It is believed that those groups are responsible for the outstanding results secured with these supports since indications are that some interaction takes place between the tinchromate-aluminum alkyl and the bound hydroxyl groups of the silica support so as to firmly anchor the tinchromate-alkyl aluminum complex on the support.

Any grade of support can be used herein but the microspheroidal intermediate density (MSID) silica is preferred for highest activity. This grade has a surface area of 258 square meters per gram and a pore diameter of about 288 A., although the intermediate density (ID) silica having the same area but a pore diameter of 164 A. is as satisfactory. Other grades such as the G-968 silica and G-966 silica-alumina, as designated by the W. R. Grace and Co., having surface areas of 700 and 500 square meters per gram, respectively, and pore diameters of 50–70 A. are also quite satisfactory. Variations in melt index control and in polymer productively can be expected between different grades of supports.

The alkyl aluminum compounds that can be used are the trialkyl aluminum compounds, the alkylaluminum halides, the alkylaluminum hydrides and alkylaluminum alkoxides. In these compounds the alkyl group can contain from 1 to about 14 carbon atoms, and the halogen can be chlorine, bromine, fluorine or iodine. Illustrative thereof are trimethylaluminum, triethylaluminum, triiso-butylaluminum, tridecylaluminum, tridodecylaluminum, diethylaluminum chloride, dibutylaluminum chloride, dibutylaluminum bromide, dibutylaluminum iodide, dibutylaluminum fluoride, dihexylaluminum chloride, methylaluminum dichloride, ethylaluminum dibromide, butylaluminum dichloride, pentylaluminum dichloride, diisobutylaluminum ethoxide and the like, as are well known in the art. They can be generically classed as compounds of the formula $R_aAlX_b$ wherein R is an alkyl group as defined above, X is hydrogen or a halogen or an alkoxy, $a$ is an integer from 1 to 2 inclusive, $b$ is an integer from 0 to 2 inclusive, and the sum of $a$ and $b$ is 3.

The mole ratio of aluminum to chromium in the catalyst system can be varied from about 2 to 1 up to about 30 to 1 or more, with preferred ratios being from about 4 to 1 up to about 15 to 1. These ratios, however, are not critical.

The concentration of tinchromate in the polymerization reaction can be varied from about 10 to about 25,000 parts per million based on the amount of olefin monomer charged, preferably the concentration is kept below about 500 parts per million.

The olefins that are ploymerized with the catalyst systems of this invention have from 2 to 8 carbon atoms and are 1-olefins and include ethylene, propylene, 1-butene, 1-pentene, 1-hexene, 4-methyl-1-pentene, 1-octene, butadiene, isoprene, piperylene, 1,3-octadiene, etc. Copolymers of two or more monomers can be so prepared according to this invention.

The homopolymers produced by the process of this invention are high density, highly crystalline products which can be used in all of those well known applications in which polyolefins are employed, for example, in the production of films, fibers, molded articles, extruded articles, coatings, and the like, and these products can then be employed in the known conventional applications therefor. The copolymers are generally less crystalline, and even amorphous, solid high polymers in some respects resembling rubbers and the like. As with other smilarly prepared copolymers, they are significantly lower in density than the homopolymers.

The polymerization reaction is carried out at temperatures of from about 30° C. or less up to about 200° C. or more, depending to a great extent on the operating pressure, olefin monomer, the particular catalyst and its concentration. Naturally, the selected operating temperature is also dependent upon the desired polymer melt index since temperature is definitely a factor in adjusting the molecular weight of the polymer. Preferably the temperature is from about 30° C. to about 110° C. in the slurry or "particle forming" technique and from 100° C. to 200° C. in "solution forming". The control of temperature in this process is desirable as hereinafter more fully described in providing various effects upon molecular weight of the polymers as well as in controlling the phase in which they are made. As with most catalyst systems, the high temperatures produce the lower weight average molecular weight ploymers and consequently of high melt index.

Regardless of whether the particle forming low temperatures or solution forming high temperatures are employed, a unique faculty of this catalyst system is the ability to carry out the polymerization to very high polymer solids, substantially higher than obtainable with any other system without fouling of the equipment.

The pressure can be any pressure sufficient to initiate the polymerization of the monomer to high polymer and can be carried out from subatmospheric pressure, using an inert gas as diluent, to superatmospheric pressure up to about 1,000,000 psig or more, but the preferred pressure is from atmospheric up to about 1000 psig. In the presence of a finely divided or large surface area support for the tinchromate to provide large surface contact of the catalyst with the monomer, pressures of 20 to 500 psig are preferred.

The inert organic solvent medium when employed in this invention is not narrowly critical but it should be inert to the catalyst and olefin polymer produced and stable at the reaction temperature used. It is not necessary, however, that the inert organic solvent medium serve also as a solvent for the catalyst composition or for the polymer produced. Among the inert organic solvents applicable for such purposes may be mentioned saturated aliphatic hydrocarbons such as hexane, heptane, pentane, isooctane, purified kerosene and the like, saturated cycloaliphatic hydrocarbons such as cyclohexane, cyclopentane, dimethylcyclopentane and methylcyclohexane and the like, aromatic hydrocarbons such as benzene, toluene, xylene and the like, and chlorinated hydrocarbons such as chlorobenzene, tetrachloroethylene, ortho-dichlorobenzene and the like.

When it is desired to conduct the polymerization to a high solids level as hereinbefore set forth, it is of course desirable that the solvent be liquid at the reaction temperature. For example, operating at a temperature less than the solution temperature of the polymer in the solvent, the process can be essentially a slurry or suspension polymerization process in which the polymer actually precipitates out of the liquid reaction medium and in which the catalyst is dissolved or suspended as finely divided mass of itself or on an insoluble support as hereinbefore set forth.

The bis(triphenyltin) chromate and the bis(triphenyltin) chromate are new compounds that utility as indicated herein each as a catalyst for polymerizing olefins particularly when used in combination with the alkyl aluminum compounds as defined herein. The following examples illustrate the principles of this invention:

Method A The tin chromate and aluminum alkyl are reacted and the reaction product is used in ethylene polymerization.

Method B The tin chromate is deposited from a solution like $CH_2Cl_2$, benzene or toluene onto high surface area silica. The dried material is used in conjunction with aluminum alkyl.

Method C The tin chromate alkyl aluminum reaction product is deposited on silica and the resulting product is used in ethylene polymerization.

Method D The silica is treated with aluminum alkyl and the reaction product is contacted with tin chromate. This mixture is used as the catalyst.

In all the methods silica was dried at 300–800° C.

Method D gave the most active catalyst. Method C gave a catalyst which was more active than B and method A was the least active. The method D catalyst composition is so active reactivities in the order of 69000g/g Cr/hr are easily realized. The ash removal is not necessary realizing savings in cost to produce polyethylene.

The bis(trimethyltin) chromate was prepared by the known method of reacting trimethyltin chloride with silver chromate. The structure of the compound was established by infrared spectrum and elemental analysis.

The new compaound bis(triphenyltin) chromate was prepared by the reaction of the triphenyltin hydroxide with chromium trioxide in refluxing methylene chloride. In a typical example a 250 ml round bottom flask was equipped with a reflux cooling condenser, heating mantle, stoppers and magnetic stirrer. The flask was charged with 175ml of $CH_2Cl_2$, 14.28g. of triphenyltin hydroxide and 16g. of $CrO_3$. This mixture was gently refluxed for 35minutes. After cooling the reaction mixture was filtered through a sintered glass funnel. Cyclohexane was added to the filtrate and the resultant yellow precipitate was isolated by filtration. The yield was 13g. The structure of the compound was established by infrared spectrm, UV spectrum (360$\mu$) and chromium analysis. It is readily soluble in benzene, toluene, etc.

Davison Chemical Company's microspheroidal silica was used after drying in air.

The aluminum alkyls triethylaluminum (TEA) and triisobutyl aluminum (TIBAL) used are manufactured by Stauffer Chemical Company. $TEA/H_2O$ (1:0.8) was prepared by adding TEA to a solution of water in benzene. TEA/EtOH (1:1) was prepared by adding ethanol to a solution of triethylaluminum.

Method A

EXAMPLE 1

In this example a Chemco reactor was used. The reactor was purged with nitrogen and brought to 60° C. reaction temperature. 0.5243g of bis(trimethyltin) chromate was added to the reactor. Triethylaluminum to give 1:2ratio of Cr:Al was added to the reactor. The reactor was closed and 300ml of a 50/50hexane/cyclohexane mmixture was pressured in. Ethylene was admitted and polymerization was started. The reactivity was 2000g/g Cr/hr.

EXAMPLE 2

In this example a one liter reactor was used. Isobutane (500ml) was the solvent. Bis(triphenyltin) chromate (0.2g) was used with triethylaluminum (Al/Cr =4). Ethylene was polymerized at 70° C. The reactivity of the catalyst was 3633g/g Cr/hr.

Method B

EXAMPLE 3

Davison Chemical 951grade silica dried at 565° C. was coated with bis(trimethyltin) chromate so as to give a 2% chromium concentration on silica. 0.3998g of this material was used in ethylene polymerization at 90° C. after promoting with triethylaluminum (Al/Cr =4). The reactivity was 11000g/g Cr/hr.

EXAMPLE 4

In this example bis(triphenyltin) chromate (20mg) deposited on one gram of Davison 952silica (dried at 800° C.) was used as the catalyst along with triethyl aluminum (Al/Cr =10). Ethylene polymerization was done at 85° C. with isobutane solvent. The reactivity was 19400g/g Cr/hr.

EXAMPLE 5

In this example conditions were the same as Example 4except the aluminum compound used was $TEA/H_2O$ (1:0.8). The reactivity was higher (25000g/g Cr/hr).

Method C

The following examples were done in isobutane solvent. The chromate was bis(triphenyltin) chromate. Silica was dried at 300° C.

| Ex. | Chromate Weight (g) | Silica (g) | Al/Cr | Aluminum Alkyl | Temp. °C. | Reactivity g/g Cr/hr |
|---|---|---|---|---|---|---|
| 6 | .2 | .87 | 2 | TEA | 85 | 12381 |
| 7 | .2 | .97 | 4 | TEA | 85 | 17491 |
| 8 | .05 | 1.17 | 10 | TEA | 70 | 20866 |
| 9 | .01 | 1.0 | 10 | TEA/$H_2O$ | 85 | 47771 |
| 10 | .01 | 1.1 | 10 | TEA/EtOH | 85 | 51332 |

$TEA/H_2O$ and TEA/EtOH were better cocatalysts.

Method D

Here, as described previously, the silica (300° C. dried) was treated with aluminum alkyl and then the bis(triphenyltin) chromate in toluene solution was added. The reaction product was used in ethylene polymerizations. The following data show that method D with TEA gave reactivitities similar to method C TEA/$H_2O$ and TEA/EtOh. The extra step of making TEA/EtOH and TEA/$H_2O$ is thus eliminated.

| Ex. | Chromate Weight (g) | Silica (g) | Al/Cr | Aluminum Alkyl | Temp. °C. | Reactivity g/g Cr/hr |
|---|---|---|---|---|---|---|
| 11 | .01 | .98 | 10 | TEA | 85 | 47413 |
| 12 | .01 | .85 | 10 | TIBAL | 85 | 69000 |
| 13 | .01 | 1.00 | 30 | TIBAL | 85 | 63200 |

The above examples show triisobutyl aluminum (TIBAL) to be more active than triethyl aluminum (TEA).

Having described my invention as related to the embodiments set out herein, it is may intention that the invention be not limited by any of the details of description, unless otherwise specified, but rather be constructed broadly within its spirit and scope as set out in the appended claims.

I claim:

1. The new compound: bis(triphenytin) chromate.
2. The new compounds: bis(tributyltin) chromate.
3. The new compounds of the class consisting of bis(tributyltin) and bis(triphenyltin) chromates.

* * * * *